(12) United States Patent
Fateh

(10) Patent No.: US 9,033,509 B2
(45) Date of Patent: May 19, 2015

(54) SYSTEM AND METHOD FOR IMPROVING THE PERIPHERAL VISION OF A SUBJECT

(71) Applicant: Atheer, Inc., Mountain View, CA (US)

(72) Inventor: Sina Fateh, Mountain View, CA (US)

(73) Assignee: ATHEER, INC., Mountain View, CA (US)

( * ) Notice: Subject to any disclaimer, the term of this patent is extended or adjusted under 35 U.S.C. 154(b) by 0 days.

(21) Appl. No.: 13/917,988

(22) Filed: Jun. 14, 2013

(65) Prior Publication Data

US 2013/0278894 A1    Oct. 24, 2013

Related U.S. Application Data

(63) Continuation of application No. 12/851,521, filed on Aug. 5, 2010, now Pat. No. 8,596,791, which is a continuation of application No. 12/353,904, filed on Jan. 14, 2009, now Pat. No. 7,789,510.

(60) Provisional application No. 61/020,970, filed on Jan. 14, 2008.

(51) Int. Cl.
*A61B 3/10* (2006.01)
*A61B 3/032* (2006.01)
*A61B 3/024* (2006.01)
*A61H 5/00* (2006.01)

(52) U.S. Cl.
CPC ............... *A61B 3/032* (2013.01); *A61B 3/024* (2013.01); *A61H 5/00* (2013.01)

(58) Field of Classification Search
CPC ........... A61B 3/024; A61B 3/032; A61H 5/00
USPC .................. 351/203, 222, 223, 224, 237, 246
See application file for complete search history.

(56) References Cited

U.S. PATENT DOCUMENTS

| 4,896,959 | A |   | 1/1990 | O'Brien |
|---|---|---|---|---|
| 5,088,810 | A |   | 2/1992 | Galanter et al. |
| 5,565,949 | A |   | 10/1996 | Kasha, Jr. |
| 5,737,060 | A | * | 4/1998 | Kasha, Jr. .................... 351/224 |

(Continued)

FOREIGN PATENT DOCUMENTS

JP            05076573 A      3/1993
KR      1020040047785        6/2004

OTHER PUBLICATIONS

Co-Pending U.S. Appl. No. 12/353,904 of Fateh, S., filed Jan. 14, 2009.
Co-Pending U.S. Appl. No. 12/851,521 of Fateh, S., filed Aug. 5, 2010.
International Search Report PCT/US2007/086413 dated May 13, 2008, pp. 1-3.

(Continued)

*Primary Examiner* — Huy K Mai
(74) *Attorney, Agent, or Firm* — Perkins Coie LLP

(57) ABSTRACT

Systems and methods for improving the peripheral vision of a subject are disclosed. In one aspect, embodiments of the present disclosure includes a method, which may be embodied on a system, for improving peripheral vision of a subject using a visual marker on a display screen, the method includes, displaying a peripheral target on the display screen, the peripheral target having a visually discernable characteristic and determining whether the subject is able to correctly identify the peripheral target displayed on the display screen using the peripheral vision. The visual marker is intended for viewing using central vision of the subject and the peripheral target is intended for identification using the peripheral vision of the subject.

46 Claims, 13 Drawing Sheets

(56) References Cited

U.S. PATENT DOCUMENTS

| | | | |
|---|---|---|---|
| 5,946,075 A * | 8/1999 | Horn | 351/246 |
| 6,260,970 B1 | 7/2001 | Horn | |
| 6,364,486 B1 | 4/2002 | Ball et al. | |
| 6,402,320 B1 | 6/2002 | Borchert | |
| 6,409,513 B1 | 6/2002 | Kawamura et al. | |
| 6,464,356 B1 | 10/2002 | Sabel et al. | |
| 6,511,175 B2 | 1/2003 | Hay et al. | |
| 7,004,912 B2 | 2/2006 | Polat | |
| 7,155,393 B2 | 12/2006 | Stewart et al. | |
| 7,326,060 B2 | 2/2008 | Seiller et al. | |
| 7,367,671 B2 | 5/2008 | Sabel | |
| 7,478,911 B2 | 1/2009 | Inakagata et al. | |
| 7,789,510 B2 | 9/2010 | Fateh | |
| 8,596,791 B2 | 12/2013 | Fateh | |
| 8,668,334 B2 * | 3/2014 | Krenik | 351/205 |
| 2009/0273758 A1 * | 11/2009 | Wang et al. | 351/243 |

OTHER PUBLICATIONS

International Search Report, PCT/US2009/000251dated Jun. 30, 2009, pp. 1-3.
Notice of Allowance Mailed Jul. 13, 2010 in Co-Pending U.S. Appl. No. 12/353,904 of Fateh, S., filed Jan. 14, 2009.
Notice of Allowance Mailed Jun. 14, 2010 in Co-Pending U.S. Appl. No. 12/363,904 of Fateh, S., filed Jan. 14, 2009.
Non-Final Office Mailed Mar. 26, 2010 in Co-Pending U.S. Appl. No. 12/353,904 of Fateh, S., filed Jan. 14, 2009.
Non-Final Office Action Mailed Mar. 19, 2013 in Co-Pending U.S. Appl. No. 12/851,521 of Fateh, S., filed Aug. 5, 2010.
Non-Final Office Action Mailed Jul. 12, 2011 in Co-Pending U.S. Appl. No. 12/851,521 of Fateh, S., filed Aug. 5, 2010.
Co-pending U.S. Appl. No. 14/050,705 by Fateh, S. filed Oct. 10, 2013.
Notice of Allowance mailed Aug. 12, 2013, for U.S. Appl. No. 12/851,521 by Fateh, S. filed Aug. 5, 2010.

* cited by examiner

SYSTEM AND METHOD FOR IMPROVING THE PERIPHERAL VISION OF A SUBJECT

CLAIM OF PRIORITY

This application is a continuation of U.S. patent application Ser. No. 12/851,521 entitled "SYSTEM AND METHOD FOR IMPROVING THE PERIPHERAL VISION OF A SUBJECT" filed on Aug. 5, 2010, which is a continuation of U.S. patent application Ser. No. 12/353,904 entitled "SYSTEM AND METHOD FOR IMPROVING THE PERIPHERAL VISION OF A SUBJECT", which was filed on Jan. 14, 2009, which claims priority to U.S. Provisional Patent Application No. 61/020,970 entitled "SYSTEMS AND METHODS TO ENHANCE VISUAL PERFORMANCE BY PRACTICING IDENTIFICATION IN PERIPHERAL VISION", which was filed on Jan. 14, 2008, the contents of which are expressly incorporated by reference herein.

BACKGROUND

Human Vision is an information-processing task. The human eyes are capable of looking at what is where but the brain processes and generates a representation of this information in its profusion of color, form, motion and detail. The central vision (center of our retina) has the highest visual acuity and discriminative vision. Visual acuity decreases with distance from the fovea (the center of the retina) to the periphery. The combined field of view of our both eyes is approximately 180° with a 120° area of overlap (FIG. 7). In general, the periphery is a larger low resolution field and the central is a smaller high resolution field.

The central area or fovea subtends only for 2.5° of our visual field but our head movements coupled with rapid eye saccadic eye movements gives the impression that the combined field of view has a resolution similar to that of the foveal resolution (high resolution). The fovea uses also these saccadic eye movements to acquire peripheral targets. A large web page, fixated at its center, creates the illusion of being equally legible all over. It is only when we maintain our focus at the center of the web page and do not shift our eyes to the edge that we realize that the periphery is illegible. Our goal is to increase and maintain the quality of this large high resolution visual field by improving identification task of the peripheral (e.g., para-central) vision.

SUMMARY

The present invention contemplates a variety of systems, apparatus, methods, and paradigms for improving the peripheral vision of a subject.

In one embodiment of the present invention, a method for improving the peripheral vision of a subject using a peripheral target displayed on a display screen is provided. The method includes practicing, by the subject, identifying the peripheral target displayed on the display screen using the peripheral vision, the peripheral target intended for identification by the subject using the peripheral vision. The method also includes determining whether the subject is able to identify the peripheral target displayed on the display screen using the peripheral vision.

The display screen may display a visual marker, the visual marker intended for identification by the subject using central vision. The method may include capturing an image or a video of an eye of the subject to detect a deviation of the central vision from the visual marker. The visual marker may be dynamic. The visual marker may be static. The visual marker may include an alphanumeric character, a shape, and/or an image. The visual marker may be in a flashing motion. The method may include changing a location on the display screen where the visual marker is located.

The appearance of the visual marker may change to a different appearance. The method may include assessing whether the subject is able to correctly identify the change of the visual marker to another visually discernible characteristic to ensure that the peripheral target is identified by the subject using the peripheral vision.

The peripheral target may have a visually discernible characteristic. The method may include determining whether the subject is able to correctly identify the visually discernible target. The peripheral target may be static. The peripheral target may be of a shape or form that includes at least one of an alphanumeric character, a shape, or an image. The identification of the peripheral target may include recognizing a particular shape or form in addition to detecting a presence of the peripheral target.

The method may include improving the peripheral vision of the subject by displaying a set of additional peripheral targets for the subject to identify using the peripheral vision, each of the set of additional peripheral targets having visually discernable characteristics, and determining whether the subject is able to correctly identify the set of additional peripheral targets in addition to detecting a presence of the set of additional peripheral targets. Each of the set of additional peripheral targets may be displayed concurrently or sequentially.

The method may include determining whether the subject is able to correctly identify the visually discernable characteristics of the set of additional peripheral targets. The method may include assessing performance of the peripheral vision by generating performance data of the subject based on whether the subject is able to correctly identify the set of additional peripheral targets or the visually discernable characteristics of the set of additional peripheral targets.

The display screen may be a computer display, a TV screen, a display of a head mounted unit, or the screen of a portable device.

The peripheral target may be dynamic.

The method may include repeating the step of the subject practicing identifying the peripheral target and the step of determining whether the subject is able to identify the peripheral target, to at least maintain a quality of the peripheral vision of the subject. The method may include repeating the step of the subject practicing identifying the peripheral target and the step of determining whether the subject is able to identify the peripheral target, to improve a quality of the peripheral vision of the subject.

In another embodiment of the present invention, an apparatus to improve peripheral vision of a user is provided, including a portable device having a display screen, the display screen configured to display multiple peripheral targets, the multiple peripheral targets intended for detection by the user using the peripheral vision, wherein a sequential or concurrent display of the multiple peripheral targets for the user to view using the peripheral vision improves the peripheral vision of the user.

The apparatus may include a performance assessment module coupled to the portable device, the performance assessment module configured to determine whether the user is able to correctly identify the peripheral targets. The apparatus may include a camera coupled to the portable device and configured to capture an image or video of eyes of a user to detect deviation of central vision of the user from a visual marker, wherein the visual marker is to be detected by the user using central vision.

The portable device may be a mobile phone. The portable device may be a head mounted unit. The portable device may be an MP3 player.

In another embodiment of the present invention, a method for displaying information is provided, the method including displaying a first information to a subject on a head mounted display, the first information being substantially in a central vision of the subject, wherein the first information is received by the subject using substantially the central vision of the subject. The method also includes displaying a second information to the subject on the head mounted display, the second information being substantially in a peripheral vision of the subject, wherein the second information is received by the subject using substantially the peripheral vision of the subject.

The first information may be static. The first information may be dynamic. The first information may include an alphanumeric character, a shape, and/or an image.

The second information may be static. The second information may be dynamic. The second information may include an alphanumeric character, a shape, and/or an image.

The first information may include game content. The second information may include game content.

The method may include capturing an image or a video of an eye of the subject. The method may include providing audible information to the subject in conjunction with displaying information.

In another embodiment of the present invention, a method for displaying information is provided, the method including displaying information to a subject on a head mounted display, the information being substantially in a peripheral vision of the subject. The method also includes leaving the central vision of the subject substantially unobstructed by the information.

The information may be static. The information may be dynamic. The information may include at least one of an alphanumeric character, a shape, or an image. The information may include game content.

The method may include capturing an image or a video of an eye of the subject. The method may include providing audible information to the subject in conjunction with displaying information.

DETAILED DESCRIPTION

Figure 1A:
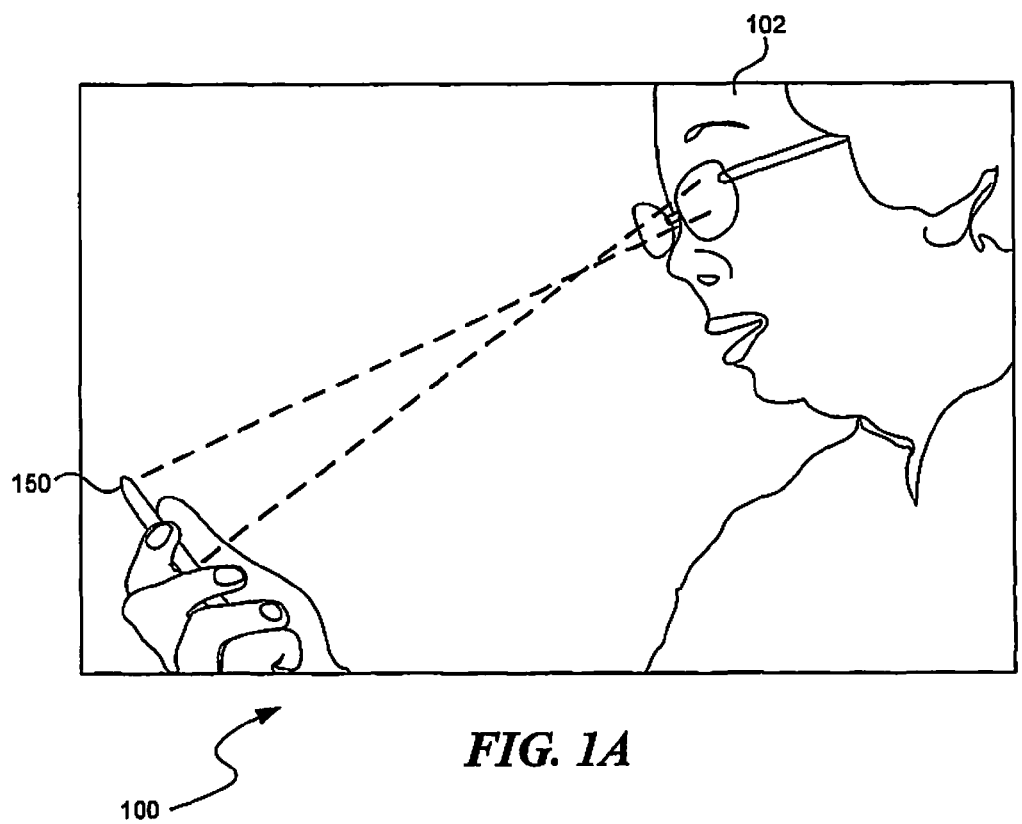
FIG. 1A depicts a diagrammatic example of a subject engaged in visual activities during a practice session using a portable device for improvement or assessment of the peripheral vision.

Embodiments of the present disclosure includes a method, which may be embodied on a system, for improving peripheral vision of a subject using a visual marker on a display screen, the method includes, displaying a peripheral target on the display screen, the peripheral target having a visually discernable characteristic and determining whether the subject is able to correctly identify the peripheral target displayed on the display screen using the peripheral vision.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Embodiments of the present disclosure include systems and methods for improving and/or assessing the peripheral vision of a subject.

Human visual acuity is predominantly contributed by the visual capability of the fovea (e.g., the center of the retina). However, the visual capability of the peripheral regions of the retina is lesser than the visual capability of the fovea and further decreases with increasing radial distance from the fovea. Thus, overall visual acuity can be increased by improving the peripheral vision of a subject.

Our natural tendency, when viewing or reading a target object large enough that fixing the fovea's central vision at one place is insufficient for visually interpreting the entire object, is to turn our eyes and our head such that our central vision can be shifted across the object for effective visual interpretation. The head movement coupled with fast eye saccadic eye movements gives the visual impression that the entire field of view is acquired using the visual capability of the fovea.

By suppressing our natural tendency to turn our head or eyes, the peripheral regions of the retina can be trained to identify objects thus improving the peripheral vision. This can be achieved by instructing the subject to stare at a visual marker that is intended for the subject to focus on using the central vision. While the subject is looking directly at the visual marker, a peripheral target is also displayed on the screen. The peripheral target is intended for identification using the peripheral vision of the subject, while the subject is directly looking at the visual marker. Identification of peripheral targets, in general, refers to recognizing characteristics of the target's characteristics (e.g., visually discernable characteristics) in addition to detecting the presence of target. This practicing task trains the subject to use visual activities to identify objects using the peripheral vision. This task also serves the purpose of assessing the subject's peripheral vision.

In addition, the user can engage in these visual activities using a portable device. For example, the visual mark and peripheral targets can be displayed in a video or an image on a computer screen, a laptop computer screen, a television set or screen, and/or portable device including but not limited to, a mobile phone, an MP3 player, a Blackberry, a Palm Treo, a handheld computer, a head mounted unit, and/or an iPhone, etc.

Generally, the peripheral target has an associated characteristic that is visually discernable. To assess the performance of the subject, the subject may be asked to identify the peripheral target and/or any visually discernable characteristics, which may be static or dynamically changing. A series of tests or practice sessions may be presented to the subject in the form of a gaming session. For example, a score indicating the performance of the user's peripheral vision can be provided at the end of each practice session. The score can be stored for multiple practice sessions such that the subject can monitor the improvement the peripheral vision.

In some instances, to ensure that the subject is identifying the peripheral target using peripheral vision, the appearance of the visual marker changes. The visual marker may also be shifted in location on the display (e.g., up, down, right, left, diagonal, etc.) during the course of a practice or examination session. The subject, in addition to being asked to identify the peripheral target, may also be asked to identify the change in appearance of the visual marker. The system can use this information to determine whether the identification of the peripheral targets was used by the subject's peripheral vision.

The techniques involved in the disclosure of peripheral vision improvement/assessment, are contemplated to be broadly applicable to treatment and/or detection of any ocular disorder and/or malfunction that involve diminished visual functions in one or more eyes and/or certain portions of the eye, and are considered to be within the scope of the novel disclosure.

FIG. 1A depicts a diagrammatic example of a subject 102 engaged in visual activities during a practice session using a portable device 150 for improvement or assessment of the peripheral vision.

The subject 102 can initiate the practice session using input controls on the portable device 150. During the practice session, the portable device 150 can visually or audibly instruct the subject 102 to look at the visual marker on the display screen. The subject looks at a visual marker intended for viewing using the subject's central vision, typically located at or near the center portions of the screen although may also be located at other portions of the screen.

The portable device 150 also displays peripheral targets that surround the visual marker generally displayed towards the edges of the display screen. The peripheral targets are intended for identification using the peripheral vision of the subject. The identification of peripheral targets using the peripheral vision can assist in the improvement and/or assessment of the subject's peripheral vision. The portable device 150 can include by way of example but not limitation, a mobile phone, a handheld computer, an MP3 player, a Blackberry, a Palm Treo, a head mounted unit, and/or an iPhone.

Figure 1B:
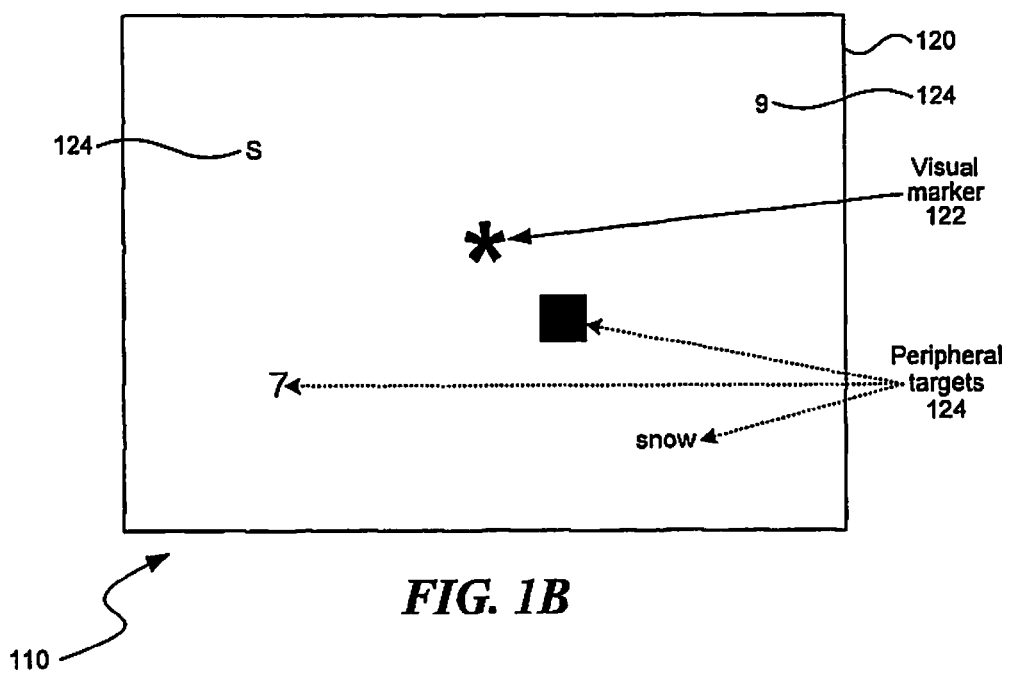
FIG. 1B depicts an example of the contents of a display screen having a visual marker and peripheral targets for identification to improve or assess the subject's peripheral vision.
Figure 5A:
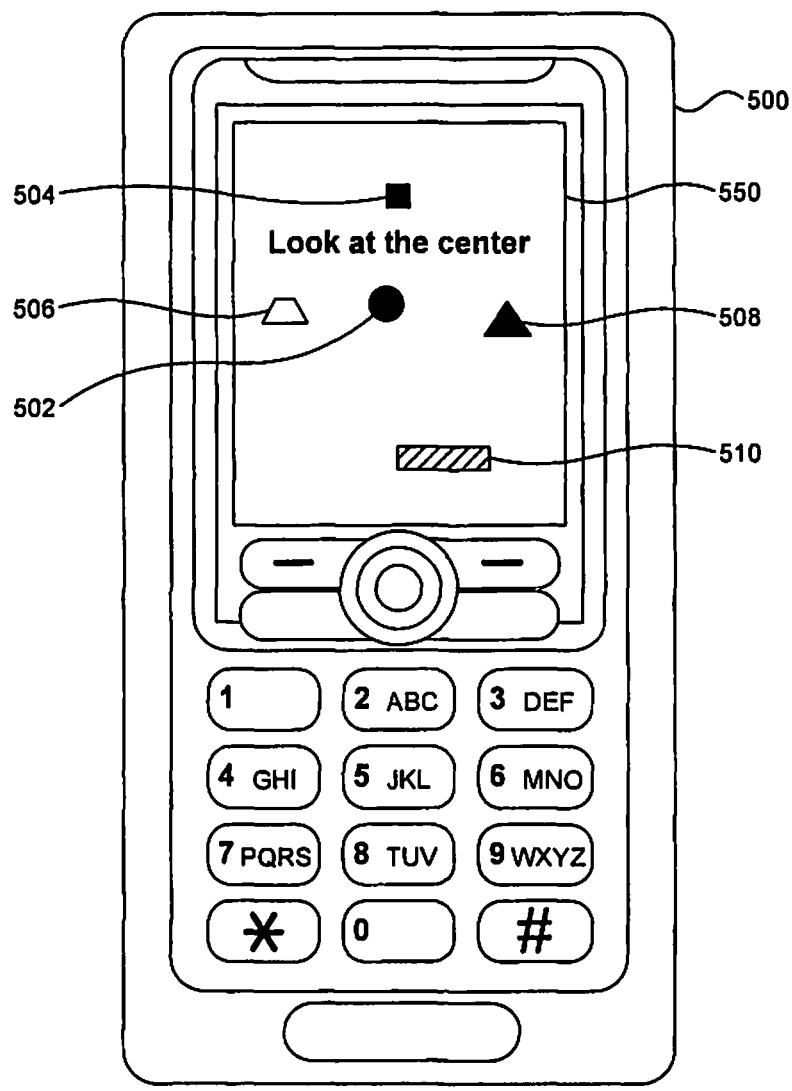
FIG. 5A-D illustrate a series of example screenshots of the display of a portable device displaying a visual marker and peripheral targets for identification by a subject during a visual activity practice session.
Figure 5B:
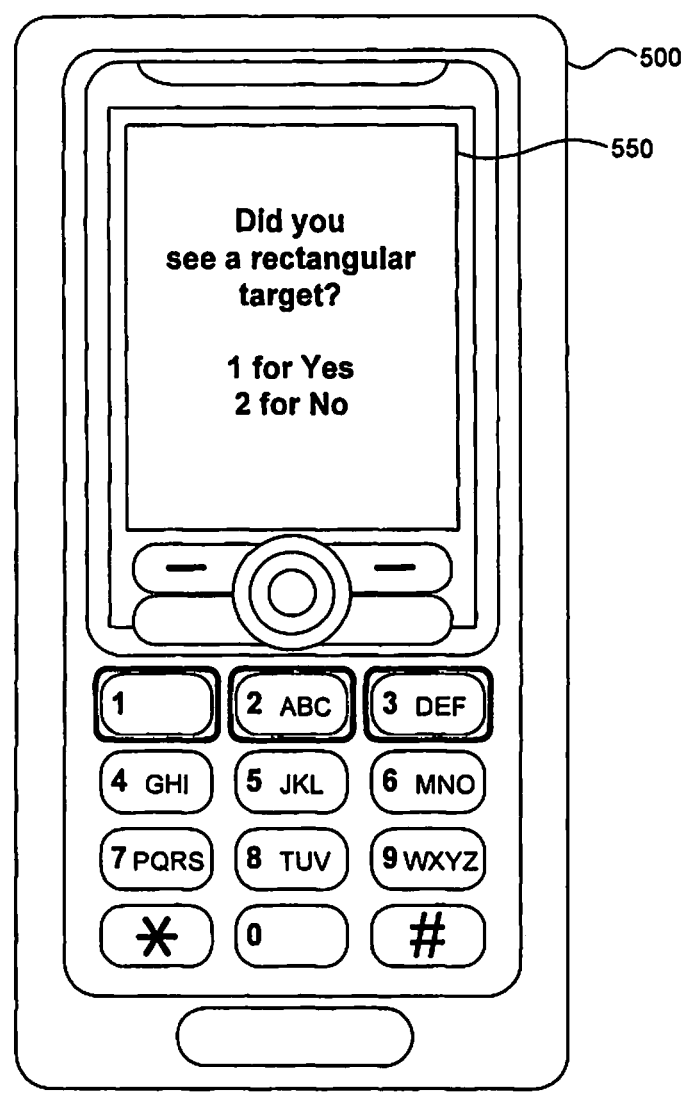
Figure 5C:
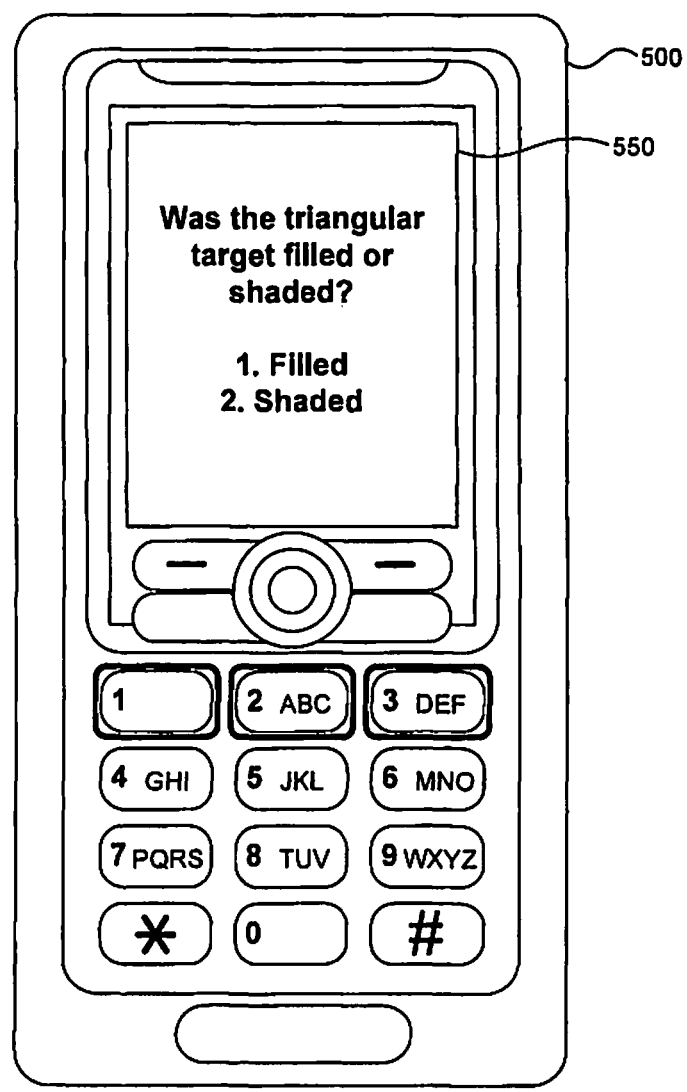
Figure 5D:
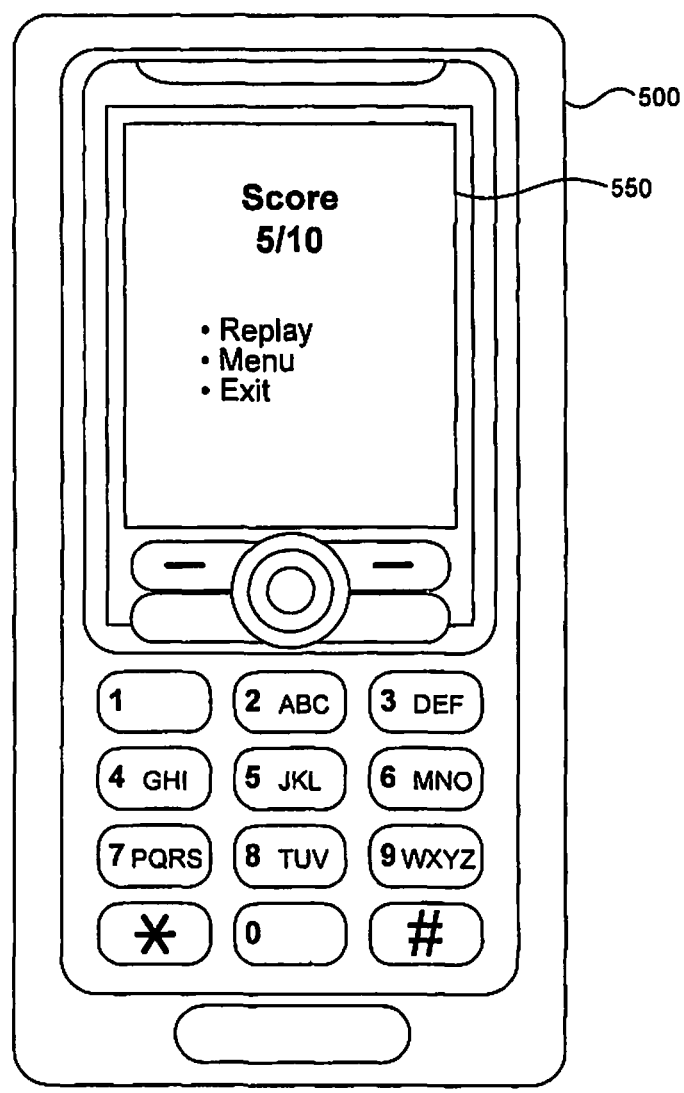
Figure 6:
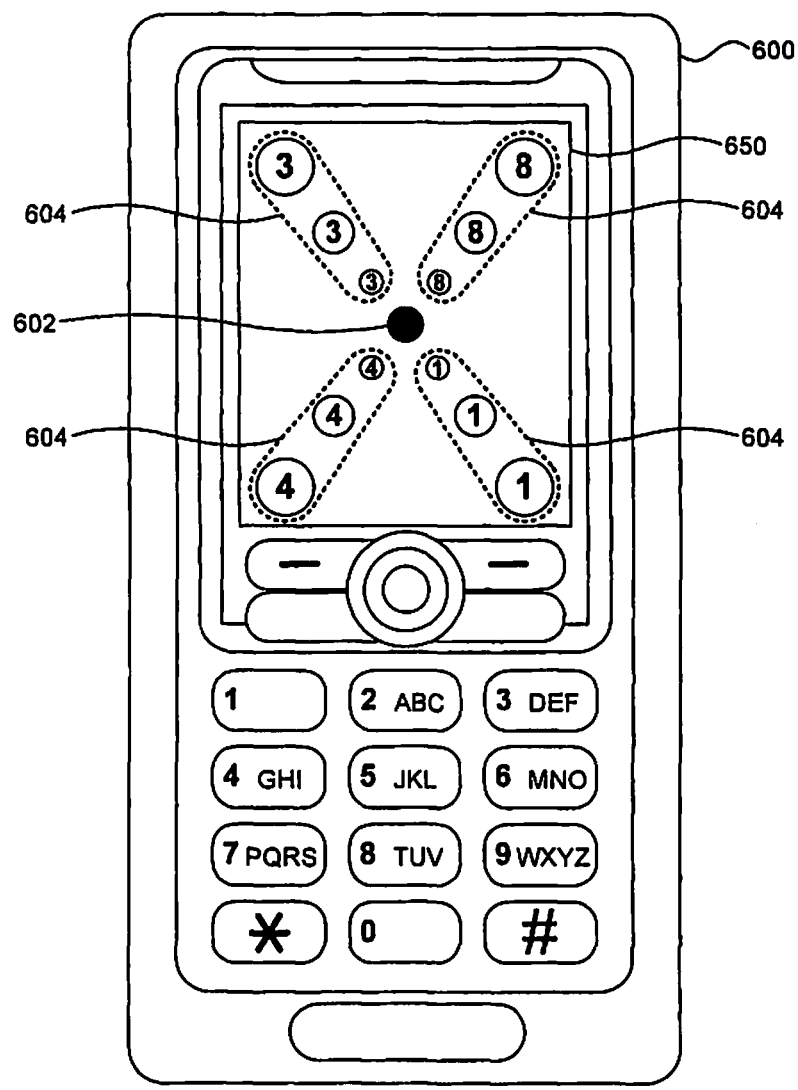
FIG. 6 illustrates another example of a screenshot of the display of a portable device displaying a visual marker and peripheral targets for identification by a subject during a visual activity practice session.

The contents of the display screens containing various visual markers and peripheral targets are illustrated in the example screenshots of FIG. 1B and FIG. 5-6.

FIG. 1B depicts an example of the contents of a display screen 120 having a visual marker 122 and peripheral targets 124 for identification to improve or assess the subject's peripheral vision.

The visual marker 122 can be displayed at or near the center portion of the display screen 120 and is intended for viewing using the subject's central vision. The visual marker 122 can also be displayed in other areas of the display screen 120, such as, to the left, right, top, or bottom of the screen 120. The visual marker 122 is illustrated in this example as having a star-like shape but can in general take upon any shape or form. For example, the visual marker 122 could be multi-colored, grey-scale, or binary-colored (e.g., black and white).

In general, the visual marker 122 can include, by way of example but not limitation, an alphanumeric character, a shape, an image, or a combination thereof. In addition, the visual marker 122 could be static or dynamically changing, such as, in flashing motion. The visual marker 122 may also change from one shape to another or from one color to another, during the course of a practice session or examination session. Note that the location of the visual marker 122 where it is displayed on the display screen 120 could also change during a particular session and/or across sessions.

The peripheral targets 124 intended for identification using the peripheral vision of the subject are typically displayed outside of the center portion and towards the edges of the display screen 120 to correspond with the peripheral regions of the retina. Such positioning of the peripheral targets 124 allows the subject to identify the peripheral targets using peripheral vision when the central vision is focused on the visual marker 122 displayed near the center or other areas of the display screen 120.

Note that each of the peripheral targets 124 has a visually discernable characteristic and may also be static or dynamically changing. In general, each of the peripheral targets 124 can include, by way of example but not limitation, an alphanumeric character, a shape, an image, or a combination thereof. The peripheral targets 124 may be displayed concurrently or sequentially depending on default settings or user preferences. The visual task of the subject in participating in the practice or examination session can include, in addition to detecting the presence of the peripheral target, identifying the peripheral target (e.g., seeing the alphanumeric character '7') and/or correctly identifying the visually discernable characteristic (e.g., detecting that the character '7' has a 'black color').

Figure 2:
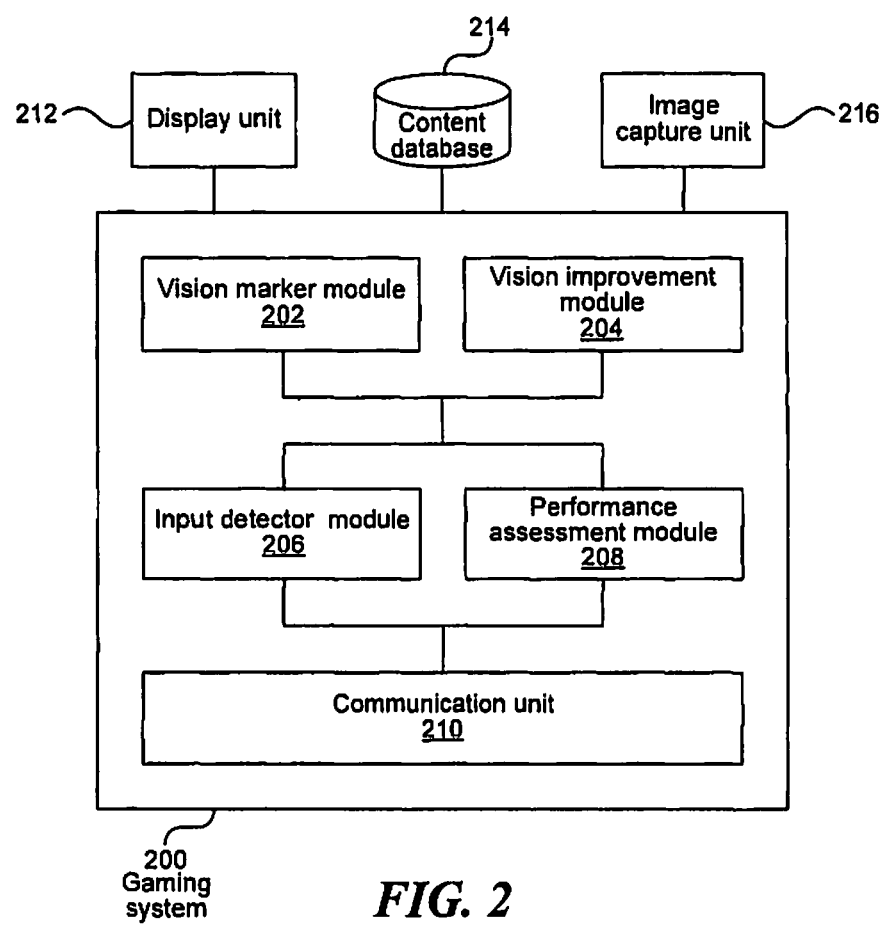
FIG. 2 depicts an example of a block diagram of a gaming system operable by a subject to engage in visual activities that improve his/her peripheral vision during a gaming or practice session.

FIG. 2 depicts an example of a block diagram of a gaming system 200 operable by a subject to engage in visual activities that improve his/her peripheral vision during a gaming or practice session.

The gaming system 200 can include a vision marker module 202, a vision improvement module 204, an input detector module 206, a performance assessment module 208, and/or a communication unit 210. The gaming system 200 may further be coupled to one or more of a display unit 212, a content database 214, and/or an image capture unit 216. In some instances, the image capture unit 216 may be internal to the gaming system 200 or coupled/internal to the display unit 212.

The display unit 212 may be a computer display (e.g., a monitor, an LCD screen, a screen of a portable computer), a TV screen (LCD, plasma, etc.), or the screen of a portable device (e.g., mobile phone, a handheld computer, MP3 player, iPhone, Blackberry, a headed mounted unit, etc.). In some instances, the content database 214 is internal or partially internal to the gaming system 200. Additional or less modules may be included in the gaming system 200.

The vision marker module 202 can be any combination of software agents and/or hardware modules able to manage, generate, modify, display, position, and/or retrieve a visual marker.

The vision marker module 202 may be coupled to the content database 214 to retrieve content including videos and/or images of visual markers for display on the display unit 212. For each gaming session or examination session where the subject is instructed to look directly at the visual marker, the vision marker module 202 can newly generate vision markers based on the particular type of game or other user preferences. For example, different types of games could display different types of characters (e.g., letters or numbers) for the subject to identify. Another type of game could display shapes with or without varying colors for the subject to identify. The sizes of the markers could be adjustable based on the vision capabilities of the subject playing the game or being examined.

In one embodiment, the vision marker module 202 selects the position on the display unit 212 where the visual marker is displayed. Since the visual marker is intended for viewing using central vision of the subject, the vision marker module 202 identifies the center point or a central portion of the display unit 212 where the visual marker can be displayed to be viewed using the subject's central vision. The vision marker module 202 can identify the center point or the center portion of the display unit 212 based on the dimensions of the display unit and the visual field of the human eye. In some embodiments, the visual marker can also be displayed in other portions (e.g., left, right, upper, lower, edge, and/or corner portions) of the display unit 212.

The vision marker module 202 manages the appearance of the visual marker during the course of a gaming session. For example, the visual marker may be static or dynamically changing (e.g., in flashing motion to attract the subject's attention). In addition, the location of the visual marker on the display unit 212 could change in time during a session or across sessions. For example, the visual marker may move across the display unit 212 in various directions (e.g., left, right, up, down, and/or diagonally) during a practice or examination session while the user continues to focus his/her central vision on the visual marker.

In one embodiment, the vision marker module 202 changes the appearance of the visual marker during a gaming session or an examination session while the subject is engaged in the visual activities to improve his/her peripheral vision. The subject's ability to detect the change in appearance ensures that the subject's central vision is focused on the visual marker and is thus using the peripheral vision to identify peripheral targets.

The vision improvement module 204 can be any combination of software agents and/or hardware modules able to manage, generate, modify, position, display, provide and/or retrieve a peripheral target.

The vision improvement module 204 may be coupled to the content database 214 to retrieve content including videos and/or images of peripheral targets for display on the display unit 212. For each gaming session or examination session where the subject is instructed to look directly at the visual marker and identify the peripheral targets, the vision improvement module 204 can newly generate peripheral targets based on the particular type of game or other user preferences. For example, different types of games could display different types of characters (e.g., letters or numbers) for the subject to identify. Another type of game could display shapes with or without varying colors for the subject to identify.

The vision improvement module 204 is, in one embodiment, coupled to the vision marker module 202 to determine the location of a visual marker on the display unit 212. Using the location of the visual marker, the vision improvement module 204 is thus operable to determine the locations where peripheral targets can be displayed on the display unit 212 during the gaming session such that the peripheral target can be identified using the peripheral vision of the subject when the user's central vision is focused on the visual marker.

In general, any object, work, image, that is not directly viewed or looked at by a user is within the user's peripheral vision. For example, the human's para-central vision is encompasses approximately 2-5 degrees about the central vision and the peripheral vision encompasses approximately any region beyond 5 degrees of the central vision.

Therefore, the location of peripheral targets relative to visual markers depends on the size of the screen and the distance of the screen from the subject's eyes. The locations can be computed on a case-by-case basis or predetermined for pre-set ranges of screen sizes since the distance of the subject's eyes generally depends on the size of the screen. Based on the location of the visual marker, the areas on the display screen covering the 5 degrees and above range of the visual field can be computed based on the screen size, and/or the distance of the user from the screen, if known.

The example screenshot of FIG. 5A illustrates the type of game with visual targets and peripheral targets of different shapes and patterns. The example screenshot of FIG. 6 illustrates a game where the peripheral targets are numbers.

The input detector module 206 can be any combination of software agents and/or hardware modules able to detect inputs of the subject before, during, and/or or after the gaming or examination session when the subject participates in visual activities or when a caregiver administers an eye exam.

During the gaming session, the subject attempts to identify the peripheral target. In addition, the peripheral target has a visually discernable characteristic that may be also identified by the subject. In one embodiment, the input detector module 206 detects selections from the subject in the subject's attempts to identify the peripheral target or attributes of the peripheral target. For example, if the subject is presented with a yes/no question (e.g., "Did you see a square target?"), the subject may be instructed to select '1' on the keyboard for 'yes' and '2' on the keyboard for 'no'. The input detector module 206 can detect the inputs and determine the selection made by the subject based on the input.

In addition, the input detector module 206 can detect user selections related to user preferences for the gaming session. In one embodiment, the subject may be able to use the keyboard to select different types of games where different types of markers and/or targets are displayed. For example, the subject may be instructed to select '1' for a game with number recognition, to select '2' for color-recognition, to select '3' for letter recognition, or to select '4' for any combination of the above. Note that the input detector module 206 may be coupled to the vision marker module 202 and/or the vision improvement module 204 such that proper markers and targets can be identified and displayed on the display unit 212 based on user preferences.

The performance assessment module 208 can be any combination of software agents and/or hardware modules able to determine a qualitative or quantitative indicator of the subject's peripheral vision based on a gaming session or an examination session.

The performance assessment module 208 is coupled to the input detector module 206 such that it can determine whether the subject had correctly identified the peripheral target on the display unit using the peripheral vision.

In one embodiment, the performance assessment module 208 is further operable to determine whether the subject is able to correctly identify the visually discernable characteristic (e.g., the color or shade) of the peripheral target. Furthermore, the performance assessment module 208 can assess whether the subject is able to correctly identify the change in the appearance of the visual marker to ensure that the subject identifies the peripheral target using the peripheral vision as opposed to the central vision. The performance assessment module 208 can use one or more of the above metrics (e.g., whether the subject identifies the peripheral target, the visually discernable characteristic of the peripheral target, and/or whether the peripheral vision was used) to generate performance data of the subject indicating the performance of the subject's peripheral vision.

The performance data may be generated on a game-by-game basis. The performance data may also be generated over specified periods of time such that the subject can track the improvement or deterioration of his/her peripheral vision.

In one embodiment, the communication unit 210 coupled to the performance assessment module 208 can be any combination of software agents and/or hardware modules able to transmit the performance data of the subject, wirelessly or via a wired connection. The performance data can be automatically or manually transmitted to the doctors' office, the hospital, the optometrist's office, or to any other caregiver.

The content database 214 can store software, descriptive data, images, system information, drivers, and/or any other data item utilized by components of the gaming system 200 for operation including archived video and/or image files comprising sets of visual markers and/or peripheral targets for display on a display screen during a practice session or examination session. In particular, the content database 214 can store visual or image content including markers and targets that have been generated or modified by the vision marker module 202 and/or the vision improvement module 204. Content stored in the database 214 can be accessible by the performance assessment module 208, the vision marker module 202 and/or the vision improvement module 204. Additionally, performance data generated by the performance assessment module 208 may be stored in the content database 214.

The database 214 be managed by a database management system (DBMS), for example but not limited to, Oracle, DB2, Microsoft Access, Microsoft SQL Server, PostgreSQL, MySQL, FileMaker, etc. The database 214 can be implemented via object-oriented technology and/or via text files, and can be managed by a distributed database management system, an object-oriented database management system (OODBMS) (e.g., ConceptBase, FastDB Main Memory Database Management System, JDOInstruments, ObjectDB, etc.), an object-relational database management system (OR-DBMS) (e.g., Informix, OpenLink Virtuoso, VMDS, etc.), a file system, and/or any other convenient or known database management package.

One embodiment of the gaming system 200 includes an image capture unit 216.

For example, the image capture unit 216 can include an electro-optical device such as a laser scanner, rasterizing laser, wand-based optical transducer one- or two-dimensional CCD, semiconductor array, vidicon, or other area imaging device (e.g., 1D imaging device, 2D imaging device) alone or coupled with software agents capable of converting received light into electrical signals. The electro-optical device in the image capture unit 216 can also include a light source such as an LED, flash bulb, infrared light source, or other light-emitting element.

The image capture unit 216 is operable to capture, track, and record images and/or videos of the subject's eyes during the gaming or examination session. The captured images and/or videos of the subject's eyes during practice or exam can be used by the image capture unit 216 to detect deviation of the central vision from the visual marker. For example, the image capture unit 216 is operable to determine whether the subject's eyes are focused and directed at the visual marker such that the central vision is focused on the visual marker rather than used to view the peripheral targets.

The image capture unit 216 can further determine the instances when the subject's eyes have deviated from the visual marker and log these instances. The image capture unit 216 may be coupled to the performance assessment module 208 to transmit data related to the instances where the subject's eye or eyes were deviated indicating irregular fixation. The performance assessment module 208 can use this data to evaluate performance of the subject's peripheral vision. In one embodiment, the gaming system is able to notify the subject in real time or near real time that his/her central vision has deviated from the visual marker.

Figure 3A:
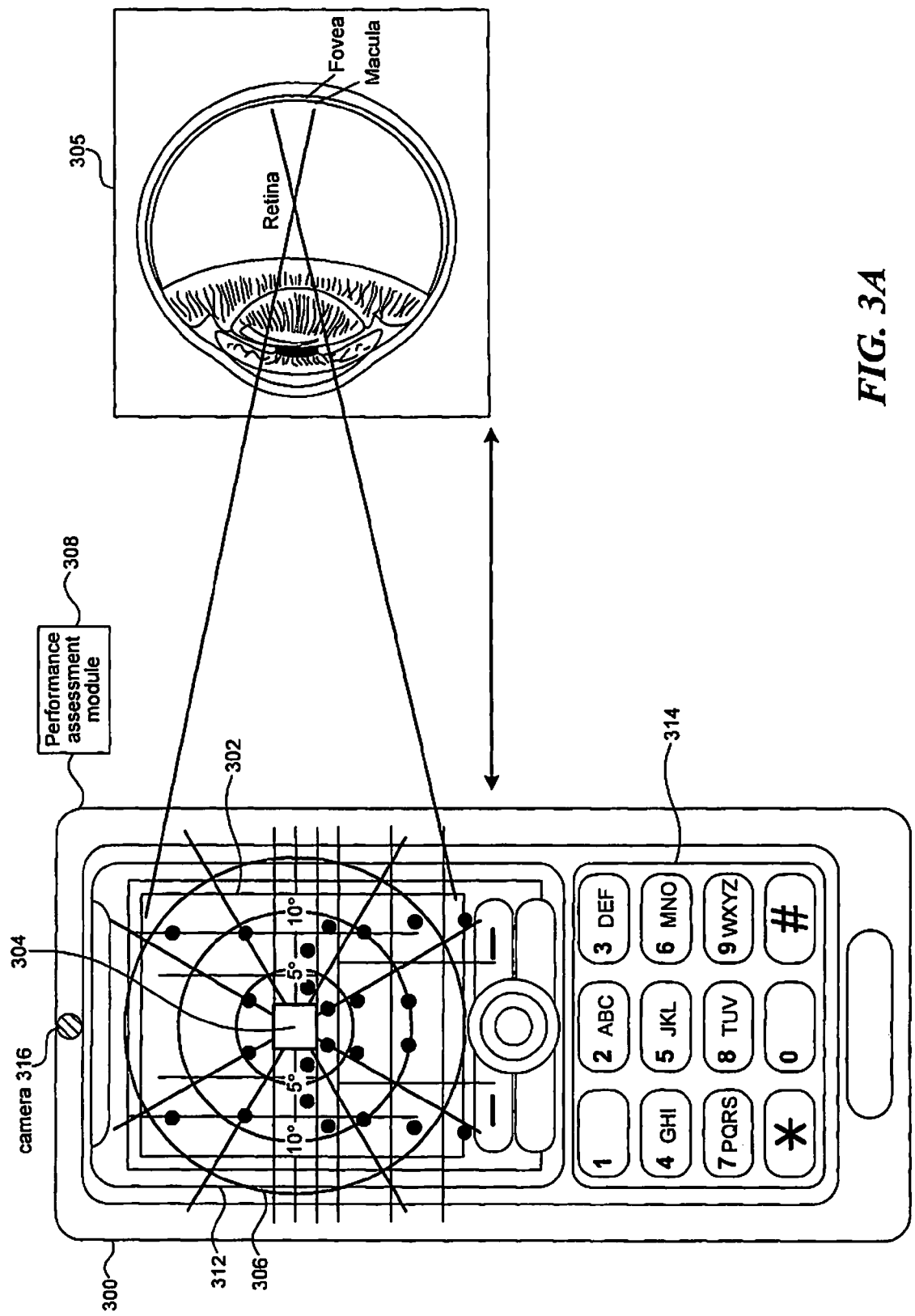
FIG. 3A depicts an example of a portable device in the field of view of a user's retina suitable for the user to engage in visual activities that can improve or assess the peripheral vision of a user.

FIG. 3A depicts an example of a portable device 300 in the field of view of a user's retina 305 suitable for the user to engage in visual activities that can improve or assess the peripheral vision of a user.

The portable device 300 includes a display screen 312 which is operable by a user to participate in the practice session to train his/her peripheral vision. The portable device 300 may further include an input selection mechanism 314 (e.g., keyboard) to the user to submit input related to the various functions and settings of the practice session.

The display screen 312 is illustrated as being overlaid with the visual field of human eyes having the central vision field 304 and the peripheral vision field 306. The portable device 300 is operable to display at least one peripheral target around or near the peripheral vision field 306 and a visual marker around or near the central vision field 304 since the visual marker is intended for viewing using central vision of the user and the peripheral target is intended for identification using the peripheral vision of the user.

Graphical depictions of the visual marker and peripheral markers on a display screen have been illustrated with further reference to FIG. 1B. Note that at approximately 30 cm distance between the display screen 312 of a typically sized portable device 300, the area of the display 312 covers approximately 5-10 degrees of the user's field of view. Since the peripheral vision of a human is typically beyond 5 degrees, the locations where peripheral targets can be placed on the display screen 312 based on where the visual marker is displayed can be computed based on an approximate distance between the screen 312 and the user's eyes.

For example, the distance between the screen 312 and the user's eyes may be estimated to be around 10-20 cm, 20-25 cm, 25-30 cm, 30-35 cm, 35-40 cm, or beyond 40 cm. The area of the display screen 312 covering the space beyond approximately 5 degrees of the visual marker can be computed to determine where peripheral targets can be displayed when the user is looking directly at the visual marker (e.g., where the central vision is focused on).

The sequential or concurrent display of the at least one peripheral targets for the user to identify using the peripheral vision during a practice session improves the peripheral vision of the user. Such sequential or concurrent display of peripheral targets allows the user to engage in visual activities using their peripheral vision. These visual activities, in addition to improving the peripheral vision of the user, allow the system to assess the performance of the user's peripheral vision and to track any improvements or degradations over time.

In one embodiment, the portable device 300 further includes or is coupled to a performance assessment module 308 that is operable to determine whether the user has correctly identified the peripheral targets and in some instances, to generate a quantitative measure (e.g., a score) indicating the performance of the user's peripheral vision. The performance assessment module 308 may be wired or wirelessly coupled to the portable device 300. The score can be computed for each practice session such that subject can monitor his/her improvement over time in identification tasks using peripheral vision.

In one embodiment, the portable device 300 includes a camera 316. The camera 316 may be built in to the portable device 300 as illustrated or externally coupled to the portable device 300. The camera 316 is operable to capture an image or video of the user's eyes to detect deviation of the central vision from the visual marker. Detection of any deviation indicates that the user may be using his/her central vision to capture the peripheral targets. This may negatively impact the score indicating performance of the user's peripheral vision. Deviation of the central vision may also negatively impact the effectiveness in training the user's peripheral vision. Therefore, the user may be notified of detection of central vision deviation such that he/she can make the necessary adjustments during the practice/examination session.

Figure 3B:
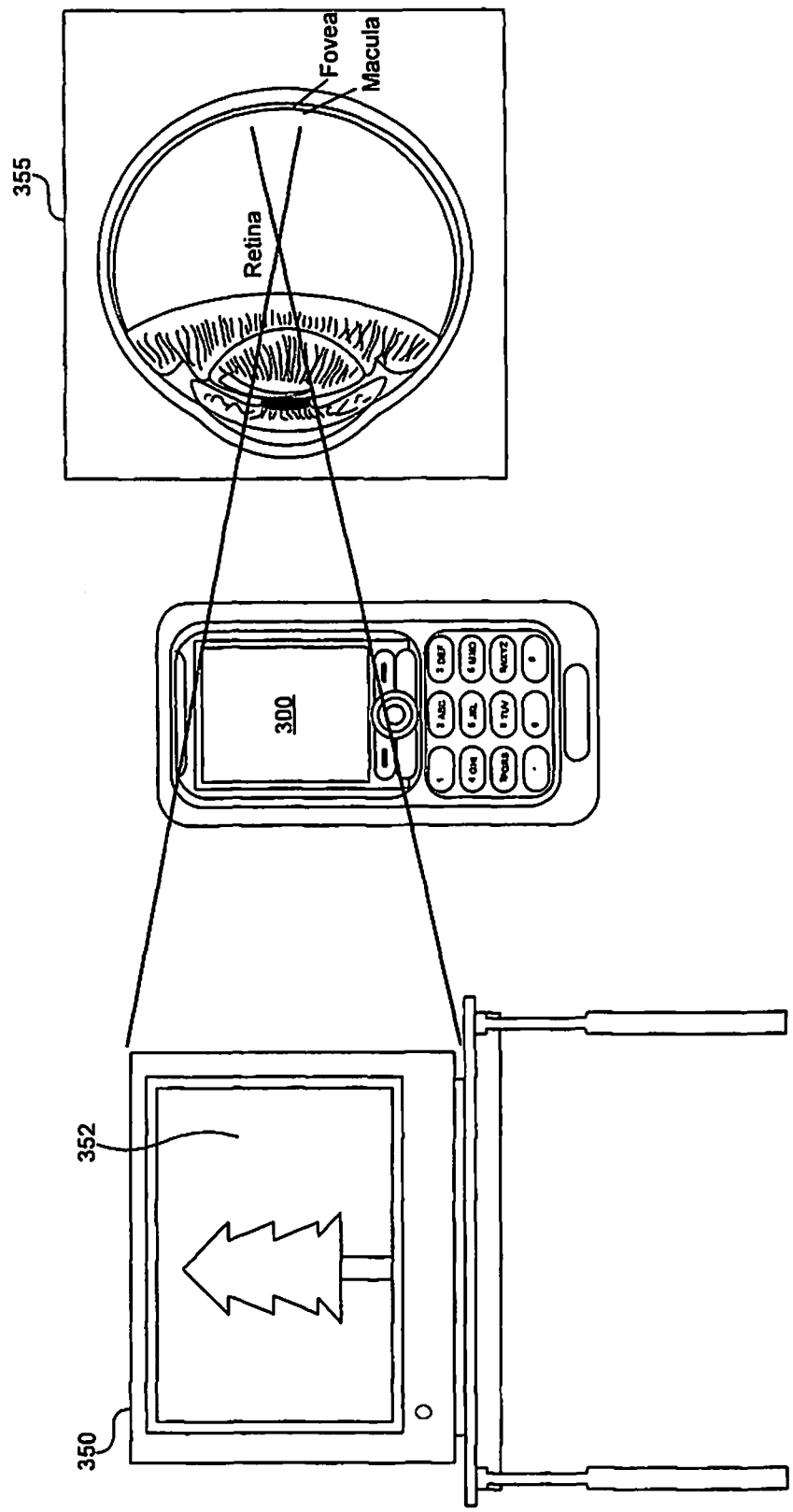
FIG. 3B depicts an example of a television screen in the field of view of a user's retina suitable for the user to engage in visual activities that can improve or assess the peripheral vision of a user.

Similarly, depicts an example of a television screen 350 in the field of view of a user's retina 355 suitable for the user to engage in visual activities that can improve or assess the peripheral vision of a user is depicted in FIG. 3B. The television screen 350 includes a display screen 352 which is operable by a user to participate in the practice session to train his/her peripheral vision or to participate in an examination session to assess the performance of the peripheral vision.

Since the peripheral vision of a human is typically beyond 5 degrees, the locations where peripheral targets can be placed on the display screen 352 based on where the visual marker is displayed can be computed based on an approximate distance between the screen 352 and the user's eyes and the area of the display screen 352.

For example, the distance between the screen 352 and the user's eyes may be estimated to be around 30-35 cm, 35-40 cm, 50-75 cm, 2-3 ft, 3-4 ft, 5-6 ft, or beyond 6 ft. The area of the display screen 352 covering the space beyond approximately 5 degrees of the visual marker can be computed to determine where peripheral targets can be displayed when the user is looking directly at the visual marker (e.g., where the central vision is focused on). Note that the distance between the screen 352 may also be estimated using the size of the screen 352 to predict where user's will sit for comfortable viewing of the screen.

Example screenshots of a display screen showing practice and/or examination sessions that a user can participate in via a portable or non-portable device are illustrated with further references to FIG. 5-6.

Figure 4:
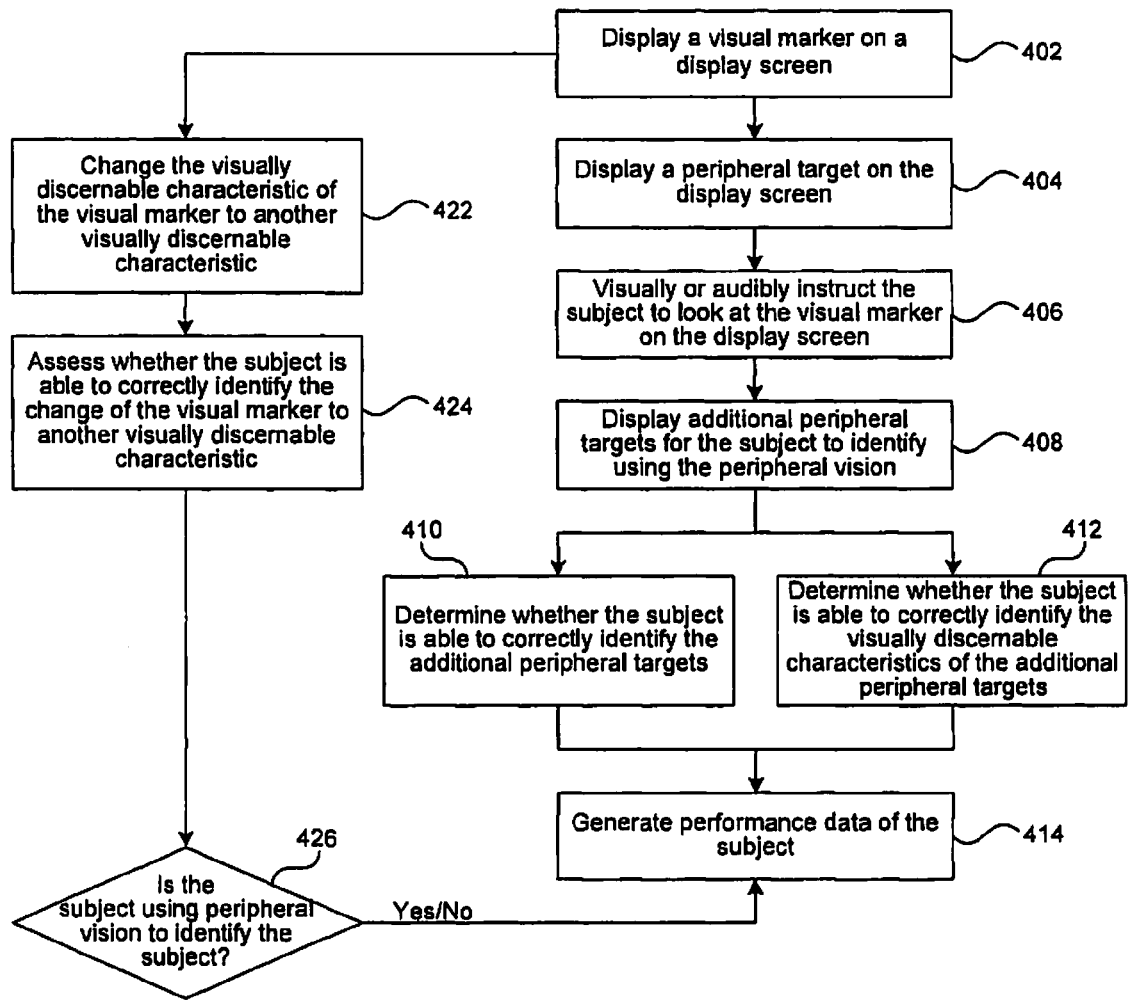
FIG. 4 depicts a flow chart illustrating an example process for improving peripheral vision of a subject using a visual marker on a display screen during a visual activity practice session.

FIG. 4 depicts a flow chart illustrating an example process for improving peripheral vision of a subject using a visual marker on a display screen during a visual activity practice session.

In process 402, a visual marker is displayed on a display screen. The visual marker may be displayed at the initiation of a practice session, gaming session, or examination session when the user engages in visual activities to improve the peripheral vision or to test the performance of the user's peripheral vision. The visual marker is located on the display screen such that it can be viewed using the subject's central vision. The visual marker can include one or more of, an alphanumeric character, a shape, or an image. In addition, the visual marker may be static of dynamically changing, for example in a flashing motion. In one embodiment, the appearance of the visual marker changes to a different appearance during a practice or gaming session.

In process 404, a peripheral target is displayed on the display screen. The peripheral target is located on the display screen such that it can be viewed by using the subject's peripheral vision while the central vision is directed at the visual marker. The peripheral target may also be one or more of, an alphanumeric character, a shape, or an image, having a visually discernable characteristic (e.g., color, shape, shade, size, etc.) and be static or dynamically changing. In one embodiment, an image or a video of an eye of the subject is optionally captured to detect deviation of the central vision from the visual marker.

In process 406, the subject is visually or audibly instructed to look at the visual marker on the display screen. Furthermore, in process 408, additional peripheral targets are displayed for the subject to identify using peripheral vision. Note that the additional peripheral targets can each be displayed concurrently or sequentially based on the type of practice session/game/exam, desired level of difficulty, default settings, and/or other user preferences. The peripheral vision can be improved when the subject identifies or attempts to identify the peripheral targets using peripheral vision.

In process 410, it is determined whether the subject is able to correctly identify the peripheral targets (e.g., whether the target is a '1" an 'A' or a 'Y') using peripheral vision. In process 412, it is determined whether the subject is able to correctly identify the visually discernable characteristics (e.g., whether the letter 'A' is white or pink) of the additional peripheral targets. In process 414, performance data of the subject is generated. The performance data can be generated based on whether the subject is able to correctly identify the set of additional peripheral targets and/or the visually discernable characteristics of the set of additional peripheral targets.

In process 422, the visually discernable characteristic (e.g., appearance) of the visual marker is changed to another visually discernable characteristic. This change can be implemented during or across practice/gaming/examination sessions. In process 424, it is assessed whether the subject is able to correctly identify the change of the visual marker to another visually discernable characteristic. In process 426, it is determined whether the subject is using peripheral vision to identify the subject. This factor can be used to compute the performance data of the subject, in process 414. For example, if the subject correctly identifies the change in appearance of the visual marker, then the system can determine that the peripheral target is identified using the subject's peripheral vision. If the change was not identified or incorrectly identified, then the subject may not have used the peripheral vision to identify the peripheral target since the subject's central vision may be shifted locations during the session.

FIG. 5A-D illustrate a series of example screenshots of the display 550 of a portable device 500 displaying a visual marker 502 and peripheral targets 504, 506, 508, and 510 for identification by a subject during a visual activity practice session.

In the screenshot of FIG. 5A, the subject is instructed to look at the visual marker 502. The visual marker 502 is concurrently displayed with 4 additional peripheral targets 504, 506, 508, and 510 intended for identification by the subject's peripheral vision.

In the screenshot of FIG. 5B, the system determines whether the subject has identified one of the peripheral targets by asking the subject "Did you see a rectangular target?" The subject can respond using the keyboard using '1' for Yes and '2' for no. In the screenshot of FIG. 5C, the system determines whether the subject identified the visually discernable characteristic (e.g., appearance) of the triangular target 508 by asking the subject "Was the triangular target filled or shaded". The subject can respond using the keyboard using '1' for Filled and '2' for Shaded.

In the screenshot of FIG. 5D, a score indicating peripheral vision performance is displayed. At this stage, the subject also has the option of repeating the same game/practice session, returning to the menu, or exiting the program.

FIG. 6 illustrates another example of a screenshot of the display 650 of a portable device 600 displaying a visual marker 602 and peripheral targets 604 for identification by a subject during a visual activity practice session. In this example, the visual marker is a black circle 602 and the peripheral targets 604 are numbers.

Figure 7:
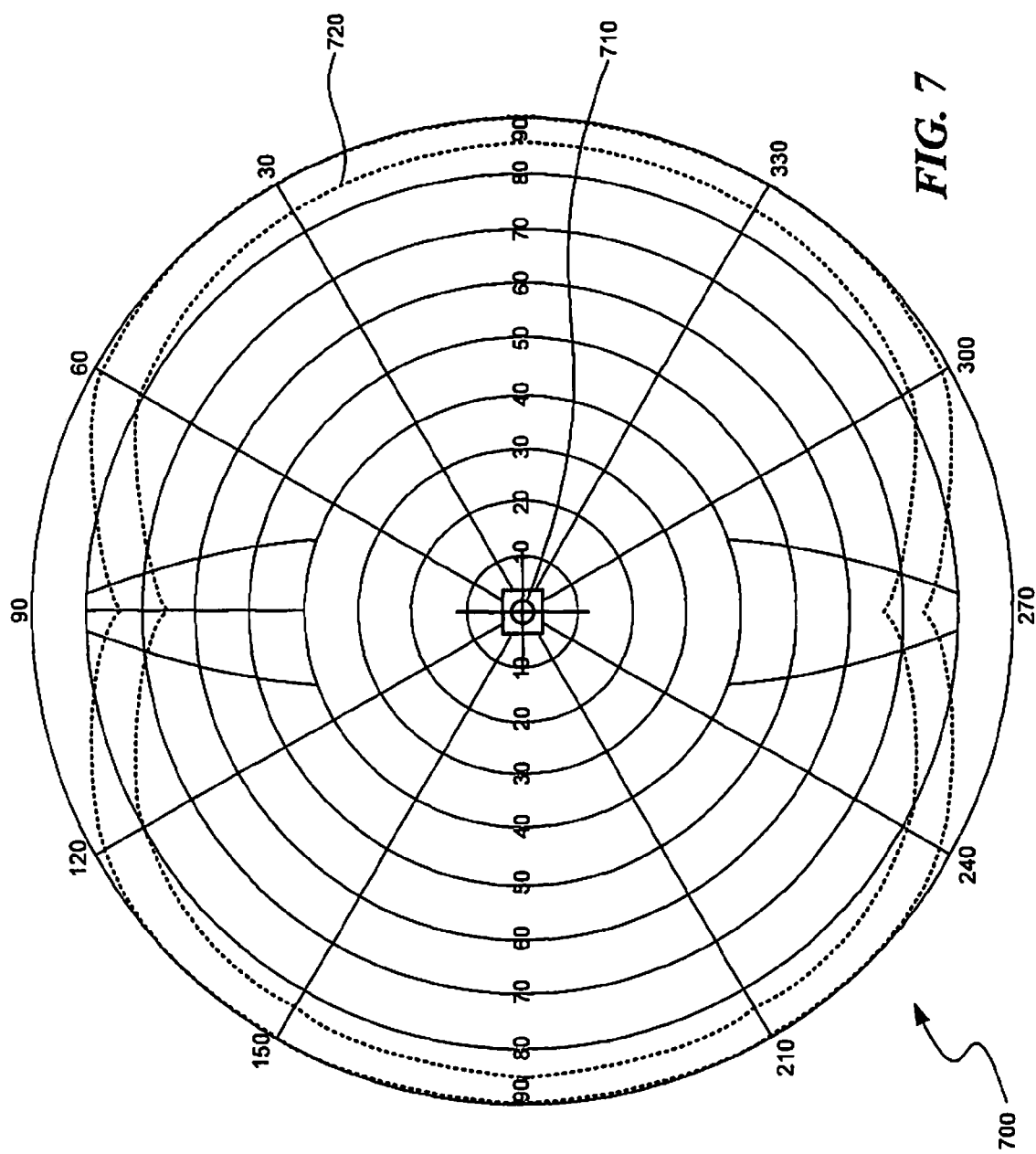
FIG. 7 depicts a diagram illustrating a map of the combined visual field of both human eyes having the central vision field and the peripheral vision field.

FIG. 7 depicts a diagram illustrating a map 700 of the combined visual field of both human eyes having the central vision field 710 and the peripheral vision field 720.

The periphery is a large low resolution field and the central is a small high resolution field. In addition, the combined visual field of both eyes is ~180°. This combined visual field generally has a ~120° area of overlap between the two eyes. The central vision field 710 provided for by the fovea subtends only for ~2.5° of the combined visual field 700 but the head movement coupled with eye saccadic eye movements gives the visual impression that field of view 700 has a foveal resolution (high resolution).

The map 700 of the visual field discriminating between the central vision field 710 and the peripheral vision field 720 allows a gaming session or practicing session for peripheral vision improvement to be designed such that the a user engages in visual activities utilizing the peripheral vision. For example, the gaming/practice/examination session can be implemented such that certain visual targets are placed in the central vision field and that certain visual targets are placed in the peripheral vision field.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or sub-combinations. Each of these processes or blocks may be implemented in a variety of different ways. Also, while processes or blocks are at times shown as being performed in series, these processes or blocks may instead be performed in parallel, or may be performed at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

Figure 8:
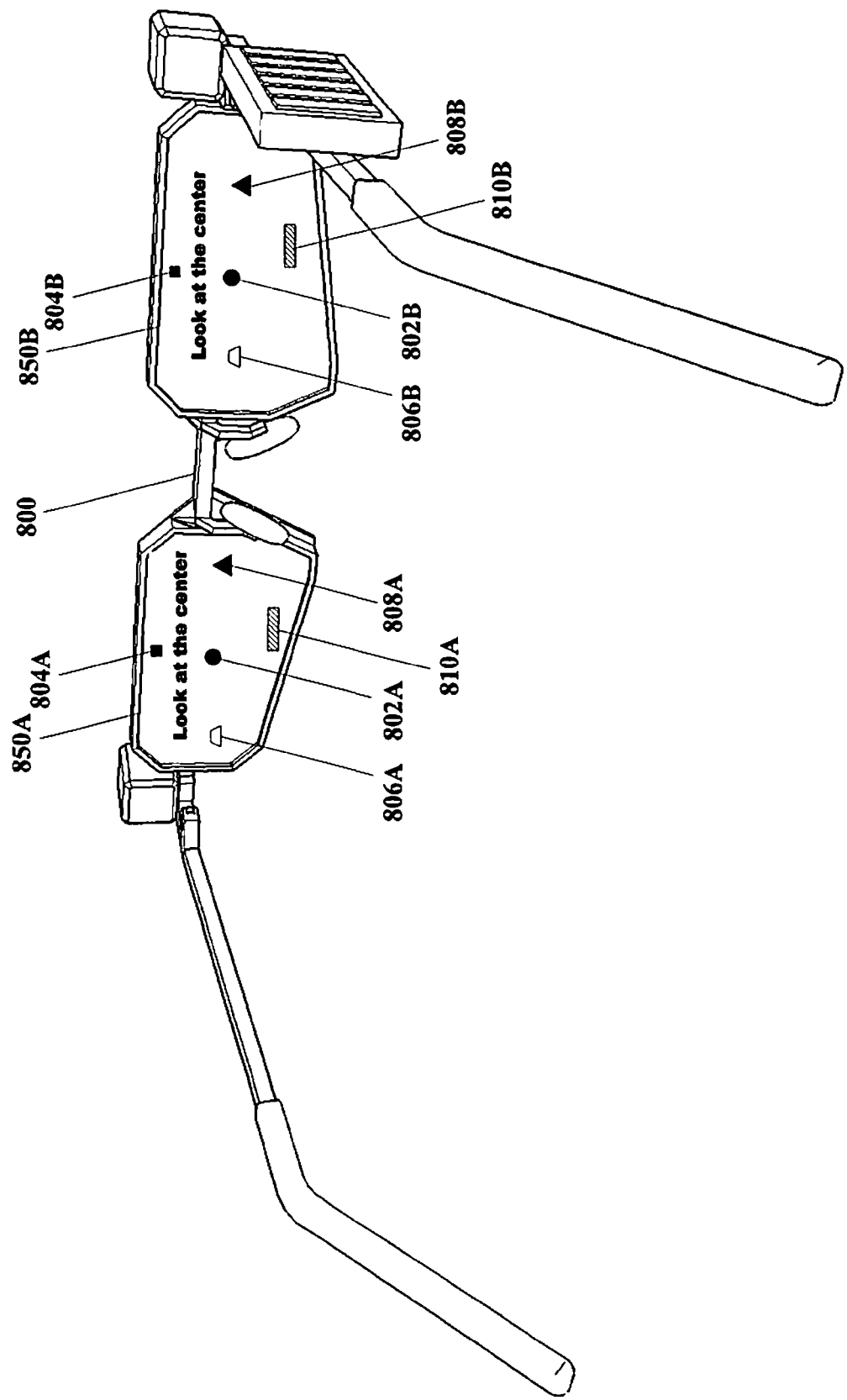
FIG. 8 illustrates an example screenshot of the displays of a portable device in the form of a head mounted display, displaying a visual marker and peripheral targets for identification by a subject during a visual activity practice.

FIG. 8 illustrates an example screenshot of displays 850A and 850B of a portable device 800, in particular a head mounted display device. Similarly to the portable device 500 in FIG. 5A as described, in FIG. 8 display 850A displays a visual marker 802A and peripheral targets 804A, 806A, 808A, and 810A for identification by a subject during a visual activity practice session. Display 850B likewise displays a visual marker 802B and peripheral targets 804B, 806B, 808B, and 810B for identification by a subject during a visual activity practice session.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. §112, sixth paragraph, other aspects may likewise be embodied as a means-plus-function claim, or in other forms, such as being embodied in a computer-readable medium. (Any claims intended to be treated under 35 U.S.C. §112, 916 will begin with the words "means for".) Accordingly, the applicant reserves the right to add additional claims after filing the application to pursue such additional claim forms for other aspects of the disclosure.

The invention claimed is:

1. A method for improving peripheral vision in a subject using a peripheral target displayed on a display screen, the method comprising:
   practicing, by the subject, identifying the peripheral target displayed on the display screen using the peripheral vision, the peripheral target intended for identification by the subject using the peripheral vision;
   the display screen displaying a visual marker, the visual marker intended for identification by the subject using central vision;
   capturing an image or a video of an eye of the subject to detect deviation of the central vision from the visual marker; and
   determining whether the subject is able to identify the peripheral target displayed on the display screen using the peripheral vision.

2. The method of claim 1, wherein the visual marker is dynamic.

3. The method of claim 1, wherein the visual marker is static.

4. The method of claim 3, wherein the visual marker is in a flashing motion.

5. The method of claim 3 further comprising:
   changing a location on the display screen where the visual marker is located.

6. The method of claim 3, wherein an appearance of the visual marker changes to a different appearance.

7. The method of claim 6 further comprising:
   assessing whether the subject is able to correctly identify the change of the visual marker to another visually discernable characteristic to ensure that the peripheral target is identified by the subject using the peripheral vision.

8. The method of claim 1, wherein the visual marker includes at least one of an alphanumeric character, a shape, or an image.

9. The method of claim 1, wherein the peripheral target has a visually discernible characteristic.

10. The method of claim 9 further comprising:
    determining whether the subject is able to correctly identify the visually discernable target.

11. The method of claim 1, wherein the peripheral target is static.

12. The method of claim 1, wherein the peripheral target is of a shape or form that includes at least one of an alphanumeric character, a shape, or an image.

13. The method of claim 1, wherein the identification of the peripheral target includes recognizing a particular shape or form in addition to detecting a presence of the peripheral target.

14. The method of claim 1, further comprising:
    improving the peripheral vision of the subject by displaying a set of additional peripheral targets for the subject to identify using the peripheral vision, each of the set of additional peripheral targets having visually discernable characteristics; and
    determining whether the subject is able to correctly identify the set of additional peripheral targets in addition to detecting a presence of the set of additional peripheral targets.

15. The method of claim 14, wherein each of the set of additional peripheral targets are displayed concurrently or sequentially.

16. The method of claim 14 further comprising:
    determining whether the subject is able to correctly identify the visually discernable characteristics of the set of additional peripheral targets.

17. The method of claim 16 further comprising:
    assessing performance of the peripheral vision by generating performance data of the subject based on whether the subject is able to correctly identify the set of additional peripheral targets or the visually discernable characteristics of the set of additional peripheral targets.

18. The method of claim 1, wherein the display screen is at least one of a computer display, a TV screen, a display of a head mounted unit, or a screen of a portable device.

19. The method of claim 1, wherein the peripheral target is dynamic.

20. The method of claim 1 further comprising:
    repeating the step of the subject practicing identifying the peripheral target and the step of determining whether the subject is able to identify the peripheral target, to at least maintain a quality of the peripheral vision of the subject.

21. The method of claim 1 further comprising:
repeating the step of the subject practicing identifying the peripheral target and the step of determining whether the subject is able to identify the peripheral target, to improve a quality of the peripheral vision of the subject.

22. The method of claim 1 further comprising:
capturing the image or video electro-optically.

23. The method of claim 1 further comprising:
capturing the image or video via laser scanning, laser rasterizing, optical transduction, one-dimensional CCD imaging, two-dimensional CCD imaging, semiconductor array imaging, and vidicon imaging.

24. The method of claim 1 further comprising:
capturing the image or video as a 1D image.

25. The method of claim 1 further comprising:
capturing the image or video as a 2D image.

26. The method of claim 1 further comprising:
capturing the image or video utilizing illumination with a light source.

27. The method of claim 1 further comprising:
capturing the image or video utilizing illumination with at least one of a group consisting of an LED, a flash bulb, and an infrared light.

28. The method of claim 1 further comprising:
capturing, tracking, and recording the eye.

29. The method of claim 1 further comprising:
capturing the image or video with a camera.

30. A portable apparatus to improve peripheral vision of a user, the portable apparatus comprising:
a portable device having a display screen, the display screen configured to display multiple peripheral targets, the multiple peripheral targets intended for detection by the user using the peripheral vision, wherein a sequential or concurrent display of the multiple peripheral targets for the user to view using the peripheral vision improves the peripheral vision of the user; and
a camera coupled to the portable device and configured to capture an image or video of an eye of the user to detect deviation of central vision of the user from a visual marker, wherein the visual marker is to be detected by the user using the central vision.

31. The portable apparatus of claim 30 further comprising:
a performance assessment module coupled to the portable device, the performance assessment module configured to determine whether the user is able to correctly identify the peripheral targets.

32. The portable apparatus of claim 30, wherein the portable device is a mobile phone.

33. The portable apparatus of claim 30, wherein the portable device is a head mounted unit.

34. The portable apparatus of claim 30, wherein the portable device is an MP3 player.

35. A portable apparatus to improve peripheral vision of a user, the portable apparatus comprising:
a portable device having a display screen, the display screen configured to display multiple peripheral targets, the multiple peripheral targets intended for detection by the user using the peripheral vision, wherein a sequential or concurrent display of the multiple peripheral targets for the user to view using the peripheral vision improves the peripheral vision of the user; and
an image capture unit coupled to the portable device and configured to capture an image or video of an eye of the user to detect deviation of central vision of the user from a visual marker, wherein the visual marker is to be detected by the user using the central vision.

36. The portable apparatus of claim 35 further comprising:
a performance assessment module coupled to the portable device, the performance assessment module configured to determine whether the user is able to correctly identify the peripheral targets.

37. The portable apparatus of claim 35, wherein the portable device is a mobile phone.

38. The portable apparatus of claim 35, wherein the portable device is a head mounted unit.

39. The portable apparatus of claim 35, wherein the portable device is an MP3 player.

40. The apparatus of claim 35, wherein:
the image capture unit comprises an electro-optical device.

41. The apparatus of claim 35, wherein:
the image capture unit comprises at least one of a group consisting of a laser scanner, a rasterizing laser, a wand-based optical transducer, a one-dimensional CCD, a two-dimensional CCD, a semiconductor array, and a vidicon.

42. The apparatus of claim 35, wherein:
the image capture unit comprises a 1D imaging device.

43. The apparatus of claim 35, wherein:
the image capture unit comprises a 2D imaging device.

44. The apparatus of claim 35, wherein:
the image capture unit comprises a light source.

45. The apparatus of claim 35, wherein:
the image capture unit comprises at least one of a group consisting of an LED, a flash bulb, and an infrared light.

46. The apparatus of claim 35, wherein:
the image capture unit is operable to capture, track, and record the eye.

* * * * *